(12) United States Patent
Li et al.

(10) Patent No.: US 8,633,133 B2
(45) Date of Patent: Jan. 21, 2014

(54) SYNTHESIS OF CLAY-TEMPLATED SUBNANO-SIZED ZERO VALENT IRON (ZVI) PARTICLES AND CLAYS CONTAINING SAME

(75) Inventors: Hui Li, Okemos, MI (US); Cheng Gu, Okemos, MI (US); Stephen A. Boyd, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 597 days.

(21) Appl. No.: 12/915,428

(22) Filed: Oct. 29, 2010

(65) Prior Publication Data

US 2011/0130575 A1  Jun. 2, 2011

Related U.S. Application Data

(60) Provisional application No. 61/256,138, filed on Oct. 29, 2009.

(51) Int. Cl.
*B01J 20/00* (2006.01)

(52) U.S. Cl.
USPC .................. 502/414; 502/526; 588/901

(58) Field of Classification Search
USPC .............. 502/407, 414, 263, 400, 526, 401; 588/316, 901
See application file for complete search history.

(56) References Cited

U.S. PATENT DOCUMENTS 6,627,084 B2 * 9/2003 Murphy et al. ............... 210/691

* cited by examiner

*Primary Examiner* — Edward Johnson
(74) *Attorney, Agent, or Firm* — Barbara J. Clark

(57) ABSTRACT

A clay comprising a 2:1 aluminosilicate clay having negative charge sites, the 2:1 aluminosilicate clay containing subnano-sized zero valent iron (ZVI) particles distributed on clay surfaces is provided. In one embodiment, at least some or all of the particles have a cross-section of five (5) angstroms or less. Methods of synthesizing and the novel clays and the clay-templated subnano-scale ZVI particles themselves are also described. Such novel products are useful in a variety of remediation applications, including for reduction and dechlorination reactions.

36 Claims, 14 Drawing Sheets

SYNTHESIS OF CLAY-TEMPLATED SUBNANO-SIZED ZERO VALENT IRON (ZVI) PARTICLES AND CLAYS CONTAINING SAME

This application claims the benefit under 35 U.S.C. 119 (e) of U.S. Provisional Application Ser. No. 61/256,138 filed on Oct. 29, 2009, which is hereby incorporated by reference in its entirety.

STATEMENT OF GOVERNMENT RIGHTS

This invention was made with government support under P42 ES004911 awarded by the National Institutes of Health. The government has certain rights in this invention.

BACKGROUND

Zero valent iron (ZVI) has been studied as a strong reductant for the environmental remediation of a wide variety of organic and inorganic contaminants including nitroaromatic compounds, uranium (VI), chromate (VI) and chlorinated organic solvents. In recent years nanoscale ZVI has gained considerable attention due to its enhanced reactivity compared to bulk or microscale iron particles.

Nanoscale ZVI is characterized by small particles having a cross section greater than 10 nm up to 100 nm, and high specific surface area, hence providing more reactive surface sites and enhanced reaction rates (1-3 order of magnitude higher) as compared with non-nanoscale ZVI.

SUMMARY

The inventors recognize the need for providing a highly reactive and efficient form of ZVI. In one embodiment, a product comprising a 2:1 aluminosilicate clay having negative charge sites, the 2:1 aluminosilicate clay containing subnano-sized zero valent iron (ZVI) particles distributed on clay surfaces, each of the subnano-sized ZVI particles having a cross-section of no more than one (1) nm or less, such as five (5) angstroms (Å) or less, is provided. In one embodiment, the 2:1 aluminosilicate clay is a swelling clay, such as smectite. In one embodiment, the smectite is montmorillonite. In one embodiment, the 2:1 aluminosilicate clay is a non-swelling clay, as the term is understood in the art, such as kaolinite (a 1:1 clay), pyrophyllite (a 2:1 clay), illite (a 2:1 clay) or combinations thereof.

In one embodiment, each subnano-sized ZVI particle comprises one or more iron atoms, such as two or more, up to several atoms. In these embodiments, each particle is essentially a cluster of atoms, with a cross section of five (5) Å or less. In one embodiment, the subnano-sized ZVI particles are intercalated in clay interlayers.

In one embodiment, a particle comprising a plurality of clay-templated subnano-sized zero valent iron (ZVI) particles, each of the particles having a cross-section of five (5) Å or less, wherein the clay is a 2:1 aluminosilicate clay (e.g., smectite clay, such as a montmorillonite) is provided. In an exemplary embodiment, the subnano-sized ZVI particles have a reactivity of greater than 90% for at least 14 days.

In one embodiment, a method comprising providing a 2:1 aluminosilicate clay template comprising layers, each layer having a substantially planar surface, wherein structural negative charges are embedded throughout each layer, embedded on each substantially planar surface, or a combination thereof; neutralizing the structural negative charges by combining the 2:1 aluminosilicate clay with exchangeable iron cations (e.g., Fe (III) or Fe(II)) to produce iron-containing 2:1 aluminosilicate clay; and reducing each of the iron-containing neutral charges with a reducing agent (e.g., borohydride salt, such as sodium borohydride or potassium borohydride) to produce subnano-sized zero valent iron (ZVI) particles having a cross section of five (5) Å or less (e.g., such as between about 3.4 and 5 Å) is provided.

The method can further comprise combining a 2:1 aluminosilicate clay with a cation to produce a homoionic 2:1 aluminosilicate clay template. In embodiments in which the exchangeable iron cations are Fe(II), the method further comprises performing the neutralizing and reducing steps in an anaerobic chamber. In one embodiment, the subnano-sized ZVI particle comprises a single iron atom having a radius of 1.72 Å.

The iron-containing 2:1 aluminosilicate clay may be in a 2:1 aluminosilicate slurry and the method further comprises adjusting the pH of the slurry to a level sufficient to prevent dissolution of the 2:1 aluminosilicate clay. In one embodiment, the pH is adjusted to about 2. The method may further comprise removing excess reducing agent.

In one embodiment, the method further comprises mixing the iron saturated clay with palladium (e.g., $Pd(NO_3)_2$) or nickel.

2:1 aluminosilicate clays, such as smectite clays, are widely distributed in the environment and inexpensive, hence offering the potential for in situ and ex situ remediation of many persistent contaminants in surface/subsurface soils and sediments. Such clays can now be used as novel templates to intercalate subnano-sized ZVI in constructed reactive domains, such as reactive caps for contaminated sediments, and reactive barrier for contaminated groundwater.

DETAILED DESCRIPTION

Figure 1:
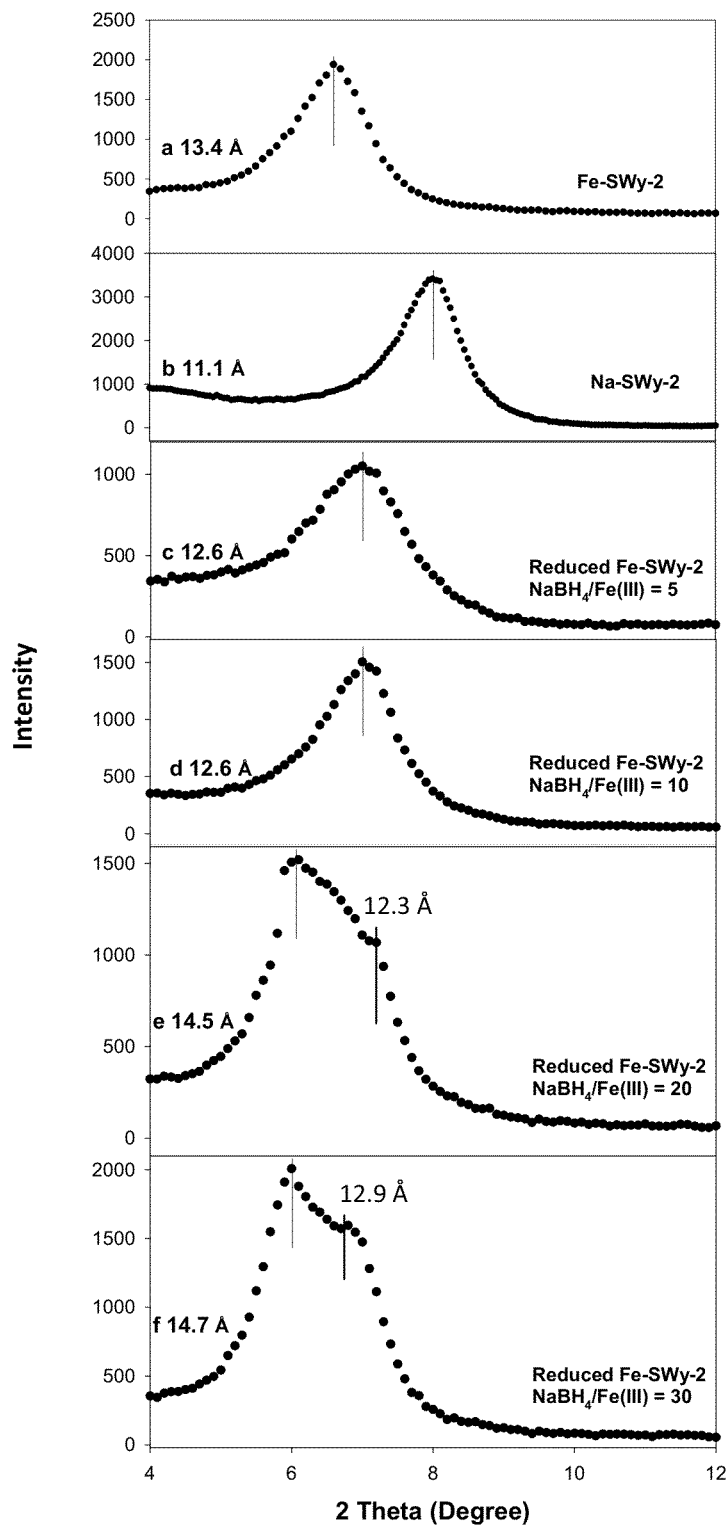
FIG. 1 shows XRD patterns of Fe-SWy-2 (curve a) and reduced iron smectite clays (curves c-f), with Na-SWy-2 (curve b) used as the reference, in embodiments of the present invention.
Figure 2:
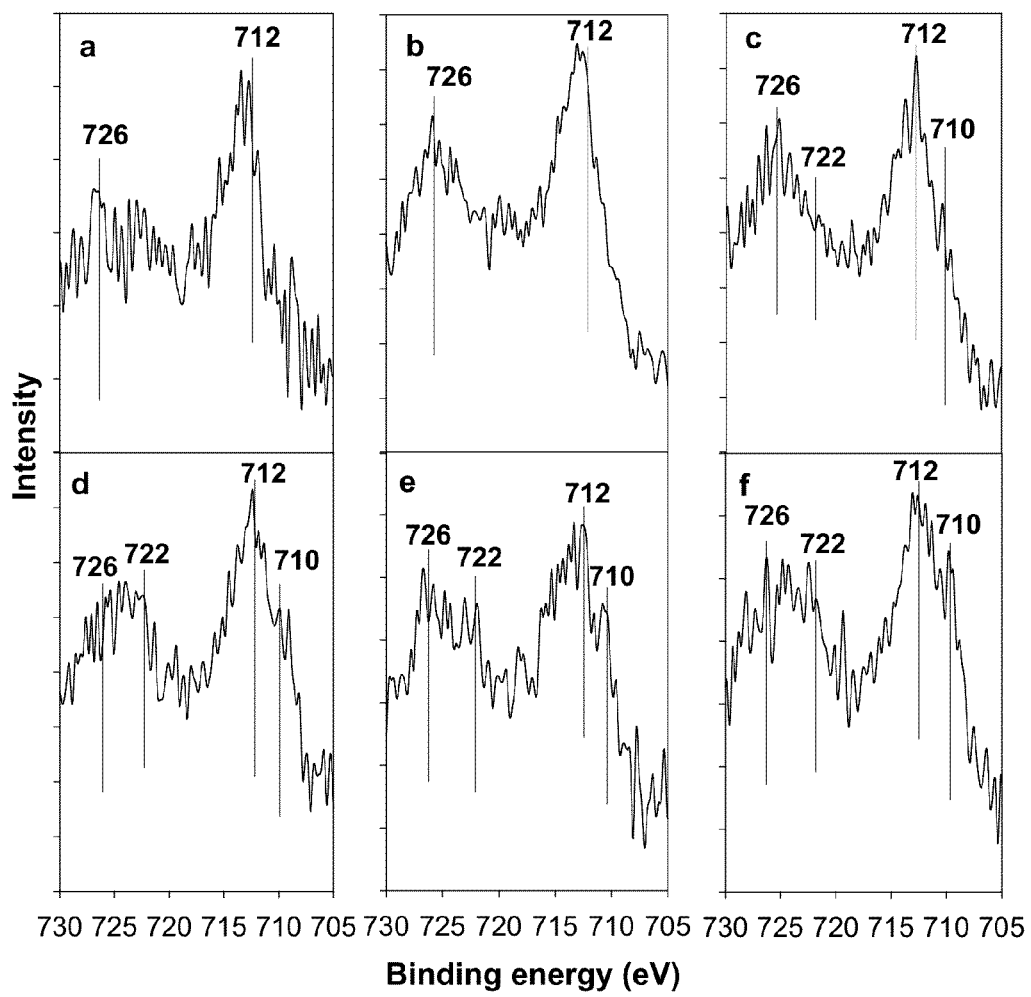
FIG. 2 shows X-ray photoelectron spectra of a) Na-SWy-2, b) Fe-SWy-2, and reduced Fe-SWy-2 at $NaBH_4$:Fe(III) ratios of c) 5, d) 10, e) 20, f) 30, in embodiments of the present invention.

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

The Detailed Description that follows begins with a definition section followed by a description of the embodiments, examples and a brief conclusion

DEFINITIONS

As used herein, the term "2:1 aluminosilicate clay" refers to a clay mineral which contains two tetrahedral silicone oxide sheets sandwiched with an aluminum oxide octahedral sheet between them. A 2:1 aluminosilicate clay belongs to a large class of sheet silicates known as phyllosilicates. Such clays can be naturally occurring or synthesized. Common naturally occurring 2:1 aluminosilicate clays include, for example, dioctahedral smectites, such as montmorillonite, beidellite, and nontronite, as well as trioctahedral smectites such as saponite and hectorite. Additional 2:1 aluminosilicates include, for example, mica, chlorite, illite, sepiolite, palygorskite, vermiculite, sauconite, and volkonskoite. Due to isomorphic substitution in the tetrahedral Si and/or octahedral Al layers, 2:1 aluminosilicate clays possess structural negative charges that are compensated by exchangeable cations (e.g., $Na^+$, $K^+$, $Ca^{2+}Mg^{2+}$) which reside at or near the clay surfaces. The types and relatives amount of exchange cations are related to the geological mechanism of clay formation.

The term is intended to further include mixtures containing a 2:1 aluminosilicate clay. Such mixtures may include materials mined from one or more geological deposits dispersed throughout the world. The Mississippi Embayment ball clays, for example, are composed of kaolinite, illite, smectite, chlorite, and other non-clay minerals such as quartz sand. These materials are known under a variety of names such as clay, bentonite, montmorillonite, smectite, ball clay, and Fuller's earth, etc., and have numerous commercial uses such as in ceramic and brick making, and as components of livestock feed, etc.

The size of the elementary platelets of 2:1 aluminosilicate clays range from a few tens to hundreds of nanometers wide and 1 to 1.8 nanometers (nm) thick. The result is a natural material with very large surface area of approximately 700 to 800 $m^2/g$. Due to isomorphic substitution in the tetrahedral Si and/or octahedral Al layers, 2:1 aluminosilicate clays possess structural negative charges that are compensated by exchangeable cations that reside at or near the negative charge sites on the clay surfaces. These layered materials most commonly occur as stacked assemblages, with the resultant formation of both external and interlayer surface area. The number of stacked layers comprising such particles depends on a variety of factors including the type of exchangeable cation, hydration status and ionic strength of aqueous solution. Depending on the type and hydration properties of exchangeable cations, the interlayer spacing is generally in the range of about two (2) to eight (8) Å when 2:1 aluminosilicate clays are exchanged with inorganic metal cations (e.g., $Na^+$, $K^+$, $Ca^{2+}Mg^{2+}$) commonly found in nature.

Additionally, there are three types of iron species associated with all 2:1 aluminosilicate clays. "Structural iron" refers to the iron species present in the Al—O octahedral sheet of smectite due to isomorphic substitution. "Exchangeable iron" is held at the external and interlayer surfaces of smectites by electrostatic interactions with the negative charges developed through isomorphic substitution. A small portion of iron may also be "complexed iron" which is complexed with surface hydroxyl groups.

As used herein, the term "homoionic 2:1 aluminosilicate clay" refers to an aluminosilicate clay whose cation exchange capacity (i.e., structured negative charge) is fully neutralized by a single type of inorganic cation such as $Ca^{2+}$ or $Cu^{2+}$.

Different forms of homoionic 2:1 aluminosilicate clays can be produced via simple cation exchange reactions. At RH≤100% homoionic K-montmorillonite, for instance, typically displays an interlayer distance of about 3 Å (up to 6 Å), and Ca-homoionic 2:1 aluminosilicate clays have interlayer distance of 8 Å or greater. The distances between adjacent exchangeable cations are not uniformly distributed and depend on layer charge density and surface area of the clay, as well as the formal charge of the cation. Such distances typically range from about 6 to 10 Å.

As used herein, the term "subnano-sized" refers to a particle having a cross-section of less than one (1) nanometer (nm). The particle may be any regular shape, such as substantially cylindrically or substantially spherical, or any type of irregular or complex shape as these terms are understood in the art. For a substantially spherically shaped particle, the diameter is less than 1 nanometer.

As used herein, the term "slurry" refers to a flowable mixture of an insoluble material (such as clay) in liquid solution (such as water).

As used herein, the term "particle" refers to a cluster of atoms, which can include one or more atoms.

DISCUSSION OF EMBODIMENTS

Iron nanoparticles have potential for both in situ and ex situ application because they can be directly injected as part of clay slurry into contaminated subsurface zones. They also can be incorporated with solid matrices, such as modified smectite clays, to achieve simultaneous reduction and adsorption capabilities.

Conventional nanoscale ZVI, however, tends to agglomerate rapidly during the synthesis process and/or application stage, resulting in larger particles with less surface area that corrode, resulting in loss of reactivity. In contrast, the novel subnano-sized ZVI particles described herein exhibit reduced corrosion, thus preserving the reactivity of the ZVI particles. The reduced corrosion is due to intercalation of the subnano-sized ZVI particles between clay layers (e.g., smectite).

In one embodiment, the intercalation in 2:1 aluminosilicate clay comprises subnano-sized ZVI particles on most of the negative charge sites. In one embodiment, more than 50% of the negative charge sites are occupied by subnano-sized ZVI particles. In one embodiment, at least 89% of the negative charge sites are occupied by subnano-sized ZVI particles. In one embodiment, all of the ZVI particles are subnano-sized. In most embodiments, the clay is provided in the form of a slurry, although the invention is not so limited. In other embodiments, the exchanged clay slurry may be dried (e.g., freeze-dried, and the like) prior to shipping, and reconstituted on site. In one embodiment, freeze-dried synthesized subnano-sized ZVI particles retains at least some, up to most, or possibly all of its reactivity over time.

In one embodiment, a novel form of ZVI is provided, which has improved reactivity and efficiency, as compared with other known forms of ZVI. In one embodiment, the novel ZVI is clay-templated subnano-sized ZVI, which comprises subnano-sized ZVI particles distributed on negative charge sites on 2:1 aluminosilicate clays.

In one embodiment, a novel method for preparing 2:1 aluminosilicate clay containing ZVI particles is provided. In one embodiment, the clay is a homoionic 2:1 aluminosilicate clay template comprising layers, each layer having a substantially planar surface, wherein structural negative charges are embedded throughout each layer, on each substantially planar surface, or a combination thereof. Stated another way, the external and interlayer surfaces of the stacked layered assemblages of the clay contain discrete negative charge sites.

In one embodiment, a novel method for synthesizing subnano-sized zero-valent iron (ZVI) particles using 2:1 aluminosilicate clays as templates (i.e., template-supporting matrices) to synthesize subnano-sized ZVI, is provided. Such clays can include various 1:1 and 2:1 aluminosilicate clays, including, but not limited to, 2:1 smectite, 1:1 kaolinite, 2:1 pyrophyllite, 2:1 illite, or combinations thereof. In one embodiment, the clay is a homoionic 2:1 aluminosilicate clay template comprising layers, as described above.

When 2:1 aluminosilicate clays, such as smectite clays, are combined or saturated (i.e., laced) with iron cations through a reduction process described herein, the cations become distributed on each of the discrete negative charge sites. As a result, the iron cations are exchanged with and neutralize the structural negative charges of the clay. In one embodiment, the exchangeable iron cations are Fe(III) cations. In one embodiment, the exchangeable iron cations are Fe(II) cations.

In one embodiment, reduction of the iron-exchanged clay with a strong reducing agent, such as a borohydride salt, results in formation of subnano-sized ZVI particles intercalated in clay interlayers. The final size and distribution of the subnano-sized ZVI particles are related to a number of factors, including, but not limited to, clay structure, origin of negative charges and surface charge density. In one embodiment, the subnano-sized particles are substantially spherical with a diameter of five (5) Å or less. In one embodiment, the subnano-sized particles are substantially spherical with a diameter between about 3.4 and five (5) Å. In one embodiment, at least some or all of the particles contain no more than two (2) iron atoms. It is also theoretically possible that at least some of the particles are single atom particles having a radius of 1.72 Å. The ability to locate ZVI on the discrete negative charge sites of 2:1 aluminosilicate clay prevents, for the first time, aggregation of iron particles during synthesis. As shown in Example 1, X-ray photoelectron spectroscopy and X-ray diffraction confirms formation of subnano-sized ZVI with the novel synthesis methods used herein.

In one embodiment, the reducing agent is a borohydride salt, such as sodium borohydride ($NaBH_4$) or potassium borohydride ($KBH_4$). In an alternative embodiment, other strong reducing agents may be used, such as sodium hydride (NaH) or sodium aluminum hydride ($NaAlH_4$). However, these chemicals are more reactive, which may require additional steps for their use herein. In one embodiment, use of excess reducing agent allows for rapid and substantially uniform growth of the synthesized ZVI particles. In a particular embodiment, excess sodium borohydride is used. Although not wishing to be bound by this proposed theory, it appears that, as compared with other synthesis methods in aqueous solution, the layered structure of the 2:1 aluminosilicate clays used herein, act as a barrier to retard the reaction between borohydrate and iron. As a result, as shown in Example 1, the excess borohydrate aided in the growth of the synthesized ZVI particles. It is likely that other reducing agents may behave similarly, such that excess amounts are desirable.

The reactivity of different forms of subnano-sized ZVI particles is determined by the magnitude and rate of reaction with probe molecules (e.g., nitrobenzene to aniline, chlorinated phenols to phenol). In one embodiment, the clay-templated subnano-sized ZVI particles exhibit superior reactivity and efficiency compared to conventional forms of ZVI, with subnano-sized ZVI particles intercalated in smectite clay manifesting the most superior reactivity. 2:1 aluminosilicate clays in which subnano-sized ZVI particles are distributed on or near most of the negative charge sites can also be considered as exhibiting superior reactivity and efficiency compared to 2:1 aluminosilicate clays which have not been exchanged by the novel methods described herein. In one embodiment, reactivity of subnano-sized ZVI particles decreases with increasing particle size. However, even the relatively larger subnano-sized ZVI particles (one (1) to five (5) nm) on mineral surfaces are highly reactive for reducing organic contaminants. In one embodiment, average particle sizes span from approximately 0.5 nm (substantially perpendicular to the clay layers) for the subnano-sized ZVI particles intercalated in smectite interlayers, one (1) to two (2) nm for the subnano-sized ZVI particles residing on kaolinite and pyrophyllite surfaces, and approximately five (5) nm for the subnano-sized ZVI particles formed on illite and smectite external surfaces.

The term "reactivity," as used herein, refers to an estimated portion of the subnano-sized ZVI particles in the clay assemblage which react with nitrobenzene, with the assumption that all exchangeable iron (e.g., Fe(III)) is reduced to Fe(0) and available to react with nitrobenzene. In one embodiment, subnano-sized ZVI particles, intercalated in smectite interlayers provided herein demonstrate an enhanced reactivity than conventional ZVI particles, at least then fold.

In one embodiment, the novel sub nano-sized ZVI (intercalated) particles manifest a high stability (i.e., reactivity of greater than 50% after exposure to air of varying relative humidities (i.e., from about five up to about 90% or higher) for several days, up to two weeks or more, possibly for as long as one to three (3) months. In one embodiment, when exposed to ambient air, the reactivity of the subnano-sized ZVI particles is preserved at levels of greater than about 90%, such as up to 99% or more for more than one day, up to several days, such as up to two weeks. In an exemplary embodiment, greater than 90% reactivity is preserved in subnano-sized ZVI particles intercalated in smectite interlayers when exposed to ambient air having a relative humidity of less than about 60%.

Use of the novel subnano-sized ZVI particles intercalated in smectite clay interlayers described herein in various applications also improves reaction efficiency of the reaction being performed. In one embodiment, reaction efficiency is up to 83% or higher which is much higher than reaction efficiencies obtained with known nano-sized ZVI particles.

In one embodiment, over 80% of nitrobenzene (2.1 mM) can be degraded within one minute with use of the novel clay-templated subnano-sized ZVI particles (Fe concentration of 0.33 g/L) prepared with a $NaBH_4/Fe(III)$ ratio of 30. In a specific embodiment, 83% of the subnano-sized ZVI particles are available to degrade nitrobenzene, i.e., the ZVI has an efficiency of 83%. Higher ZVI reaction efficiencies are also possible if reaction conditions are optimized, such as up to 89% or greater, such as 90% or more.

In one embodiment, smectite clay-templated subnano-sized ZVI particles can also be used to degrade chlorinated aromatic compounds, such as chlorophenols and chlorinated dioxins (e.g., octachlorodibenzo-p-dioxin).

In one embodiment, a bimetallic system is used in order to increase the dechlorination reactivity of ZVI. In such embodiments, palladium (Pd) or nickel (Ni) is used as a catalyst. Generally, sufficient Pd is added to improve the efficiency of the reaction, so that reaction time is reduced about 100 to 1000 times (as compared to conventional dechlorination treatments using ZVI devoid of Pd and Ni). In one embodiment, the concentration Pd in clay is about 0.65 mg Pd per gram of 2:1 aluminosilicate clay. In such embodiments, the bimetallic subnano-sized ZVI is synthesized as described in Example 2. It is expected that Ni will speed the reaction in a similar fashion.

The invention will be further described by reference to the following examples, which are offered to further illustrate various embodiments of the present invention. It should be understood, however, that many variations and modifications may be made while remaining within the scope of the present invention.

Example 1

Materials and Methods

Chemicals

Sodium borohydride ($NaBH_4$, >98%), anhydrous ferrous chloride ($FeCl_2$) (>99.99%), nitrobenzene (>99.5%), nitrosobenzene (>97%) and aniline (>99%) were obtained from Sigma-Aldrich (Milwaukee, Wis.) Anhydrous ferric chloride ($FeCl_3$) and sodium phosphate dibasic ($Na_2HPO_4$) were purchased from Fisher Scientific (Fair Lawn, N.J.). Acetonitrile was of HPLC-grade. All the chemicals were used as received.

Standard

Wyoming montmorillonite (SWy-2), a smectite clay, was obtained from the Source Clays Repository of the Clay Minerals Society (Purdue University, West Lafayette, Ind.). Na-SWy-2 and Ca-SWy-2 were prepared according to the method of Arroyo et al., *A simple method for partial purification of reference clays, Clays and Clay Miner.* 2005, 53, 511-519, which is incorporated by reference as if fully set forth herein. In this method, negatively-charged sites are compensated with $Na^+$ and $Ca^{2+}$, respectively. The total iron contents in these two clays represent only the "structural iron," as defined above. The cation exchange capacity (CEC) and theoretical surface area of SWy-2 are 82 $cmol_c/kg$ and 750 $m^2/g$, respectively.

Preparation of Subnano-Sized ZVI

The preparation of Fe(III)-montmorillonite from SWy-2 followed the method of Arroyo et. al., supra. Briefly, the clay suspension was first titrated to pH 6.8 with 0.5 M sodium acetate buffer (pH 5) to remove carbonate impurities. Clay-sized particles (<2 μm) were obtained by centrifugation for 6 min at 60 g, followed by treatment with 0.1 M $FeCl_3$ solution. The Fe(III)-SWy-2 was washed using Milli-Q® brand water (Millipore Corporation, Bedford, Mass.), until free of chloride, as indicated by a negative test with $AgNO_3$. The washed Fe(III)-SWy-2 was stored at 4° C. as an aqueous suspension for further use.

Fe(II)-montmorillonite was also prepared following the same method, except that $Fe^{2+}$ in $FeCl_2$ was used exchangeable cation in the preparation, and the experiment was conducted inside an anaerobic chamber (Coy Laboratory Products, Grass Lake, Mich.).

Before reduction by $NaBH_4$, the pH of the Fe(III)-montmorillonite slurry was adjusted to approximately 2 using 1 M HCl. Upon addition of $NaBH_4$, the clay immediately turned to black color, indicating that Fe(III) was reduced to Fe(0). The molar ratio of $NaBH_4/Fe(III)$ (based on interlayer iron species) was adjusted from 1.5 to 35. To remove the excess of $NaBH_4$, the clay suspension was centrifuged and rinsed with Milli-Q® brand water.

Characterization of Subnano-Sized ZVI

The Fe and Na contents in clay were determined via acid digestion and inductively coupled plasma-optical emission spectrometry by Huffman Laboratories, Inc. (Golden, Colo.). Clay basal spacings were measured by X-ray diffraction (XRD) analysis. The X-ray diffractometer was equipped with CuKα radiation (λ=1.5418 Å) and crystal graphite monochromater, operating at 45 kV and 100 mA. The diffraction patterns were collected between 4 and 12° at a scanning rate of 1°/min. All the samples were freeze-dried before the XRD analysis.

Transmission electron microscopy (TEM) images were examined using a JEOL 2200FS 200 kV field emission microscope coupled with a X-ray energy dispersive spectroscopy (X-EDS) system (Oxford instrument, UK). The X-EDS elemental mapping was performed in the scanning transmission mode with INCA acquisition software (Oxford instrument, UK). For analysis by TEM and X-EDS, a carbon-coated 300 mesh grid (Electron Microscopy Sciences, Fort Washington, Pa.) was used. The copper grid was dipped into clay suspensions containing Fe-SWy-2 clays before and after $NaBH_4$ reduction. The dipped copper grids were then air-dried inside the anaerobic chamber (Coy Laboratory Products, Grass Lake, Mich.). To confirm the reduction of Fe(III) to Fe(0), X-ray photoelectron spectroscopy (XPS) (Perkin-Elmer Physical Electronics PHI5400 spectrometer) was employed with a monochromatic Mg X-ray source operated at 30 kV and 300 W with an emission current of 20 mA. After reduction, the clay was directly deposited I the sample chamber to avoid re-oxidation.

Determination of Reduction Efficiency

The reaction efficiency of synthesized ZVI was studied using nitrobenzene as the "probe molecule". The amount of the probe molecule nitrobenzene reduced to aniline was used to estimate the amount of electrons transferred from ZVI to nitrobenzene, hence the reaction efficiency of ZVI. The degradation experiments were carried out in 7-mL glass scintillation vials. To each vial, 0.02 mL of nitrobenzene methanol stock solution (0.4%) was added to freshly synthesized clay suspension (5 mL, clay content was 12.6 g/L based on dry weight) to obtain an initial nitrobenzene concentration of 2.1 mM. All water used in the experiment was Milli-Q water, and was fully deoxygenated by purging with $N_2$ for 1 hr. Reaction vials were then placed on a rotary shaker (Thermo Scientific LabQuake Tube Shaker/Rotator, Fair Lawn, N.J.) inside the anaerobic chamber. After 3 hrs, approximately 2 mL of clay suspension was immediately filtered through 0.45 μm regenerated cellulose syringe filter (Whatman, Dassel, Germany).

Nitrobenzene and other reaction products (nitrosobenzene, phenylhydroxylamine and aniline) were analyzed by a reverse-phase high-performance liquid chromatography (HPLC) system (Perkin-Elmer, Norwalk, Conn.) fitted with a 15 cm×4.6 mm Discovery C18 column (Sigma-Aldrich/Supelco, Supelco Park, Bellefonte, Pa.). An isocratic mobile phase comprising a mixture of acetonitrile/aqueous 20 mM $Na_2HPO_4$ (pH=7) (55:45, v/v) was used at a flow rate of 1 mL $min^{-1}$. The UV wavelength for detection was set at 240 nm for aniline and phenylhydroxylamine, and at 272 nm for nitrobenzene and nitrosobenzene.

The experiments were conducted in triplicate at room temperature (approximately 23° C.). Experimental controls consisted of $Na^+$- and $Ca^{2+}$-saturated montmorillonites subjected to the same methods as compared to Fe(III)-montmorillonite. Fe(II)-SWy-2 was used to investigate the reactivity of surface and interlayer-bound $Fe^{2+}$ species upon the reduction of nitrobenzene.

Results and Discussion
Characterization of Subnano-Sized ZVI

As noted in the definition above, there are three types of iron species associated with 2:1 aluminosilicate clays, such as the montmorillonite clay used herein, i.e., structural, exchangeable and complexed. A comparison of iron content with Na- and Ca-SWy-2 clays was performed, with the assumption that total iron contents in these two clays represent only structural iron.

As shown in Table 1 below, the structural iron content in each of the reference clay specimens, Na- and Ca-SWy-2 clays, is about 2.6%, which is in agreement with the literature. In both Fe(III)- and Ca-SWy-2, negligible amounts of sodium were present. However, after Fe(III)-SWy-2 was reduced by $NaBH_4$, the sodium content increased dramatically. As the $NaBH_4$/Fe(III) ratio increased from 1.5 to 35, the sodium content increased from 1.32 to 2.5%.

This increase occurred because, as Fe(III) was reduced to Fe(0), negative charges associated with clay minerals (once balanced by Fe(III)) were now compensated by $Na^+$ from the added $NaBH_4$. The total iron content in Fe-SWy-2 was about 6%, including 2.6% of structural iron and 3.4% of non-structural iron content.

Based on the CEC value (82 $cmol_c$/kg) of SWy-2 clay, the calculated Fe content originating from exchangeable Fe(III) is approximately 1.5%, indicating that some other forms of iron are also present. It is likely that iron oxyhydroxide precipitates or other iron species with less overall charge (i.e. less than +3) may also be associated with the clay when preparing Fe-smectite clay.

It is known that the amounts and speciation of iron intercalated in smectite clays are strongly dependent on pH, temperature and "aging" time, i.e. time elapsed after the preparation process, with iron content reported as high as 26 mmol/g clay with a OH/Fe ratio of 2. Under the conditions present in this testing, the pH of 0.1 M $FeCl_3$ was approximately 1.7, so it is unlikely that precipitation and hydroxylation of Fe(III) occurred. However, during the washing steps the pH was neutralized to 4.5. Therefore, it is likely Fe(III) in the clay interlayer may have formed small oligomers, e.g. $Fe(OH)^{2+}$, $Fe_2(OH)_2^{4+}$ and $Fe_3(OH)_4^{5+}$. This would account for the higher than expected iron loading on SWy-2 based on its CEC. The iron content in the synthesized ZVI in clay assemblages did not change significantly with the increase of $NaBH_4$/Fe(III) ratio and dropped from 5.99% to 5.28%, suggesting that a small portion of iron was released from clay upon the reduction by $NaBH_4$ and subsequent rinsing with water. See Table 1 below.

TABLE 1

Total Iron and Sodium Contents of Montmorillonite (SWy-2) Saturated with Different Exchangeable Cations

| Smectite | Total Fe Content (wt %) | Total Na Content (wt %) |
|---|---|---|
| Fe-SWy-2 | 5.99 ± 0.01 | 0.039 ± 0.001 |
| Ca-SWy-2 | 2.60 ± 0.02 | 0.085 ± 0.004 |
| Na-SWy-2 | 2.67 ± 0.01 | 2.57 ± 0.02 |
| FeSWy-2 after $NaBH_4$ reduction | 5.28 ± 0.19 | 1.24 ± 0.03 to 2.50 ± 0.15 |

Preliminary results indicate that when the pH of Fe-SWy-2 was higher than 4, $NaBH_4$ reduction reaction was significantly slowed. If excessive acid was added resulting in the pH<1, the clay itself could be dissolved and the synthesized ZVI might react with acid. In our experiments, the pH was adjusted to about 2 before the addition of $NaBH_4$, and the final pH was 7.5 to prevent dissolution of the clay and reaction of the synthesized ZVI with acid, and further to depolymerize molecular weight hydroxyl-iron polymers.

The formation of ZVI from Fe(III) proceeded according to the following reactions:

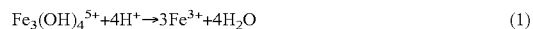

$$Fe_3(OH)_4^{5+} + 4H^+ \rightarrow 3Fe^{3+} + 4H_2O \tag{1}$$

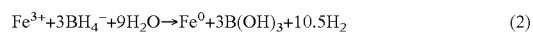

$$Fe^{3+} + 3BH_4^- + 9H_2O \rightarrow Fe^0 + 3B(OH)_3 + 10.5H_2 \tag{2}$$

Initially, the low molecular weight hydroxyl-iron polymer, e.g. $Fe_3(OH)_4^{5+}$ depolymerizes to release Fe(III), which is then reduced to Fe(0) by $NaBH_4$.

The XRD patterns of original (curve a) and reduced iron montmorillonite clays are shown in FIG. 1 (curves "c" through "f"), with Na-SWy-2 used as the reference montmorillonite clay (curve "b"). 2θ represents the diffracted angle relative to the incident X-ray beam. Basal spacing of air-dried Fe-SWy-2 is 13.4 Å (curve "a") is consistent with the presence of a monolayer of the small iron oligomeric intercalates. After the clay was reduced at $NaBH_4$/Fe(III) ratios of 5 and 10 (curves "c" and "d", respectively), diffraction peak became broader and less intense, indicating the collapse of some interlayer regions, manifesting a d-spacing of 12.6 Å. After reduction with $NaBH_4$, the exchangeable cations in the clay interlayer are thought to be $Na^+$ ions, since exchangeable Fe(III) in Fe(III)-SWy-2 has been reduced to ZVI.

At more intensive reduction with $NaBH_4$/Fe(III) ratios of 20 and 30 (curves "e" and "f", respectively), the basal spacing increased to approximately 14.5 Å. Such spacing is an indicative of intercalation of iron clusters in the clay interlayers. Assuming the thickness of the montmorillonite sheet is 9.6 Å (as is known in the art), then the size of formed ZVI is approximately 5 Å. This size is one to two times smaller than nanoscale ZVI synthesized from conventional methods. The small shoulders at 12.3 and 12.9 Å in curves "e" and "f" can be explained by the replacement of Fe(III) with $Na^+$, causing the collapse of clay interlayers. The lack of a peak at 2θ of 44.9° in XRD spectrum (diffraction of crystalline phase of Fe(0) at this angle) suggests that there is no continuous Fe(0) phase in the clay interlayer.

Due to the low iron content in Fe-SWy-2 smectite clay, the Fe 2p signals in the XPS spectra of both the original (FIG. 2B) and reduced Fe-clay (FIG. 2A) are relatively weak. The peaks at binding energies of Fe $2p_{1/2}=726$ eV and Fe $2p_{3/2}=712$ eV represent the oxidized iron species, and two peaks at Fe $2p_{1/2}=722$ eV and Fe $2p_{3/2}=710$ eV correspond to ZVI. Compared to the XPS spectra of original Na-SWy-2 and Fe-SWy-2 (FIG. 2A), the Fe(0) peaks in the spectra of reduced Fe-SWy-2 gradually become more intense as the increase of $NaBH_4$:Fe(III) ratios, indicative of more ZVI present at higher level of reduction (FIGS. 2C-2F).

Figure 3A:
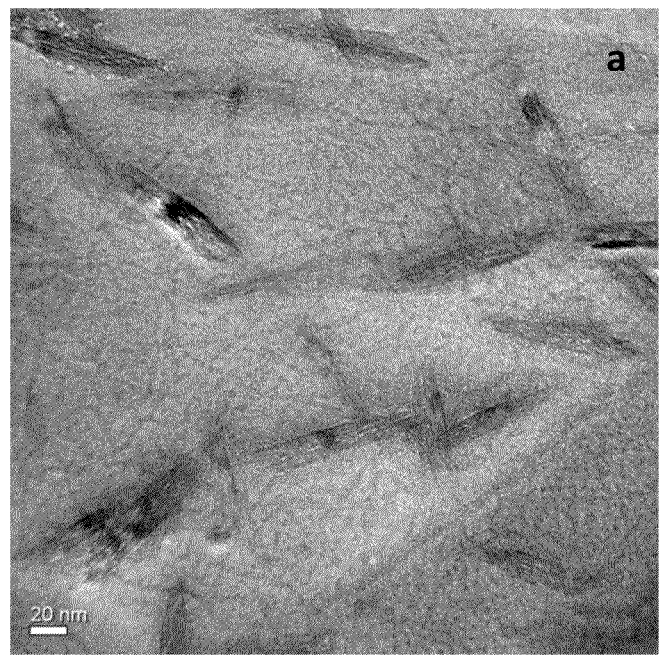
FIG. 3A is a transmission electron microscopy image of Fe-SWy-2 clay in an embodiment of the present invention.
Figure 3B:
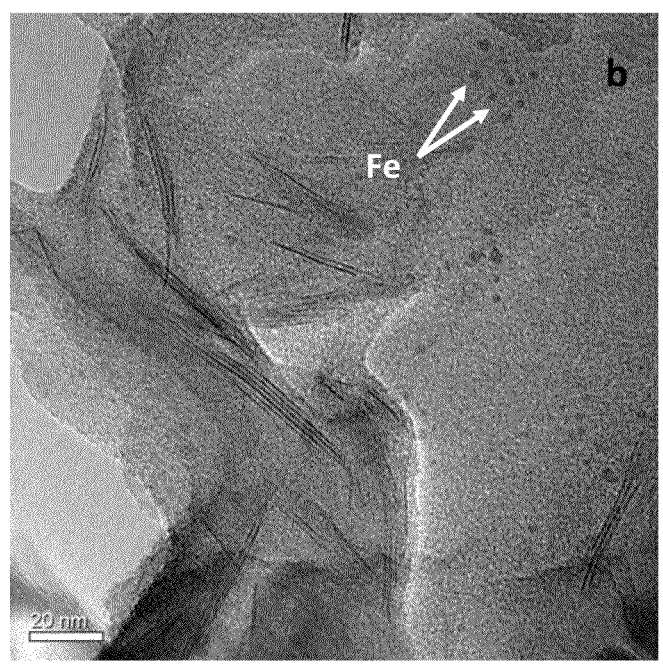
FIG. 3B is a transmission electron microscopy image of reduced Fe-SWy-2 by $NaBH_4$ ($NaBH_4$:Fe=3.5) in an embodiment of the present invention.

The TEM images of Fe-SWy-2 and reduced Fe-SWy-2 are presented in FIGS. 3A and 3B, respectively. The pristine Fe-SWy-2 clay in FIG. 3A shows a well-developed crystalline layer structure with thickness and length of about 12 and 65 nm, respectively. The stacked layered structures of Fe-SWy-2 are clearly visible prior to reduction with $NaBH_4$. As shown in FIG. 3B, after reduction ($NaBH_4$:Fe=3.5), the layered structures are much less evident, and the clay platelets in general appear more disordered (i.e. less stacking), each unit with different and fewer clay layers.

This visualization is in agreement with the broad peak in the XRD spectrum (curve "c" in FIG. 1), which is due to the lack of structural constancy. Reduced iron particles of around 3 nm in diameter (highlighted by arrows in FIG. 3B) are visible on the exposed external planar surfaces of the clay. Iron particles inside the clay interlayers cannot be directly observed by TEM, but X-EDS elemental mapping for Fe-SWy-2 before and after $NaBH_4$ reduction both clearly demonstrated that the distribution of Fe(0) is closely related to that of clay structural Al and Si (data not shown), suggesting that reduced Fe is evenly distributed on the internal surfaces of the clay.

Reduction Efficiency of Subnano-Sized ZVI in Clay

It is known that both structural and surface-bound iron species demonstrate strong reduction potential for nitroaromatic compounds when $Fe^{3+}$ was reduced to $Fe^{2+}$. However, the control experiments described herein showed negligible degradation of nitrobenzene for Ca- and Na-SWy-2 after mixing with $NaBH_4$ and washing with deionized water. This result indicates that structural iron present in the aluminosilicate structure of SWy-2 clay does not participate in the reduction of nitrobenzene. In addition, during the time frame of the experiment (approximately 3 hrs), there was no detectable degradation of nitrobenzene in the presence of Fe(II)-saturated SWy-2, which may rule out the possible nitrobenzene reduction contributed from $Fe^{2+}$ species on the clay. These results indicate that the reactive iron species in the novel system results primarily from the ZVI in the interlayer or on the clay surface (although in some embodiments, complexed iron may be present, although likely on the order of less than 10% or even lower), since the $Fe^{2+}$ cannot reduce nitrobenzene.

The sorption of nitrobenzene and aniline by SWy-2 clays was insignificant (<5%). Therefore, the reactivity and efficiency of ZVI reduction was estimated by directly measuring nitrobenzene and aniline concentrations in the aqueous phase.

The reduction of nitrobenzene follows the reductive reaction pathway shown below:

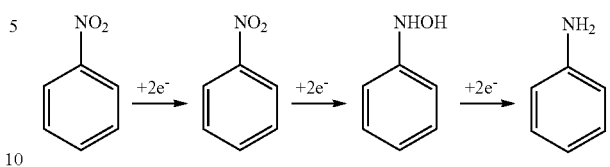

in which the final reduction product is aniline. Nitrosobenzene and phenylhydroxylamine are partially reduced intermediates.

The initial concentration of nitrobenzene used in this testing was 2.1 mM. It was assumed that the total exchangeable iron content in the clay could be reduced to ZVI and available for reduction of nitrobenzene to aniline. Therefore, the amount of aniline formed in the experiments can be used to measure the efficiency of synthesized ZVI. Kinetic experiments indicated that the degradation of nitrobenzene occurred rapidly, i.e., within the first minute; the first sampling of reaction mixture showed the reduction of nitrobenzene to phenylhydroxylamine and aniline. As the reaction proceeded, phenylhydroxylamine was reduced to aniline, which accumulated as the major reductive product. After about two hours, the reaction reached equilibrium, with most of the phenylhydroxylamine having been converted to aniline (>98%), in addition to a small amount of nitrosobenzene (<1%). Equilibrium was reached within three (3) hours.

Figure 4:
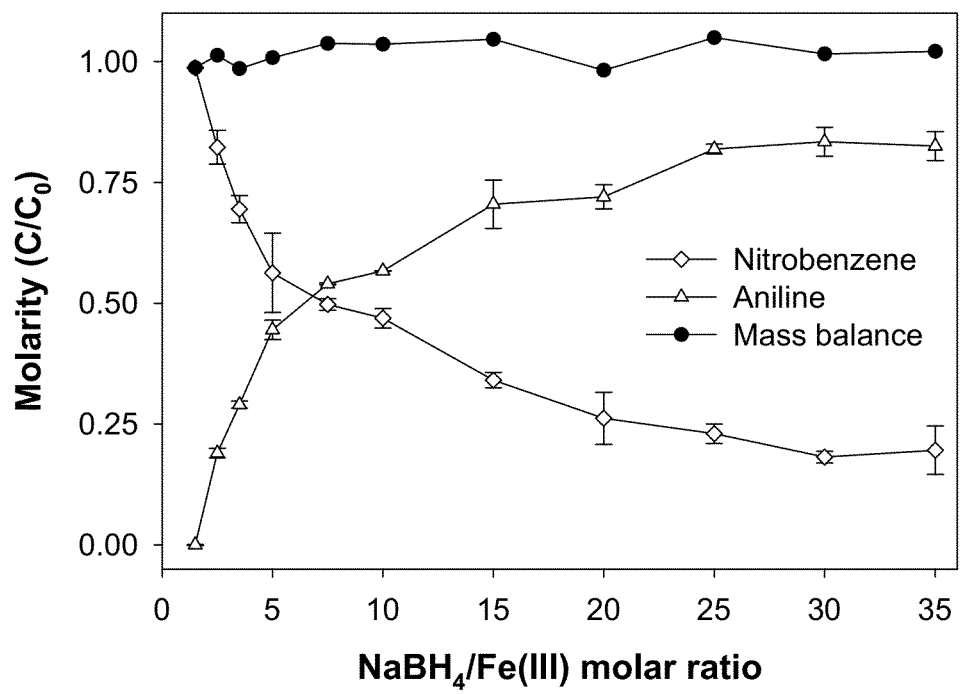
FIG. 4 shows the reduction efficiency of synthesized subnano-sized zero valent iron (ZVI) templated in smectite interlayers at different $NaBH_4$/Fe(III) molar ratios in embodiments of the present invention.

FIG. 4 shows the reduction efficiency of synthesized subnano-sized ZVI templated in smectite interlayers at different $NaBH_4$/Fe(III) molar ratio. (As noted above, experimental conditions: initial nitrobenzene, clay and interlayer iron concentrations of 2.1 mM, 12.6 and 0.33 g/L, respectively. Error bars are the standard deviations of triplicate analyses). As the results show, the reduction efficiency, as dictated by the normalized molarity of aniline increased as the $NaBH_4$/Fe(III) molar ratio, increased from 1.5 to 25. At that point, the reaction reached a plateau with maximum efficiency of approximately 83%. At lower $NaBH_4$/Fe(III) ratio, only partial exchangeable iron could be reduced, which could be interpreted as the lower reaction efficiency. As more borohydrate was used, more Fe(III) was converted to ZVI.

Figure 5:
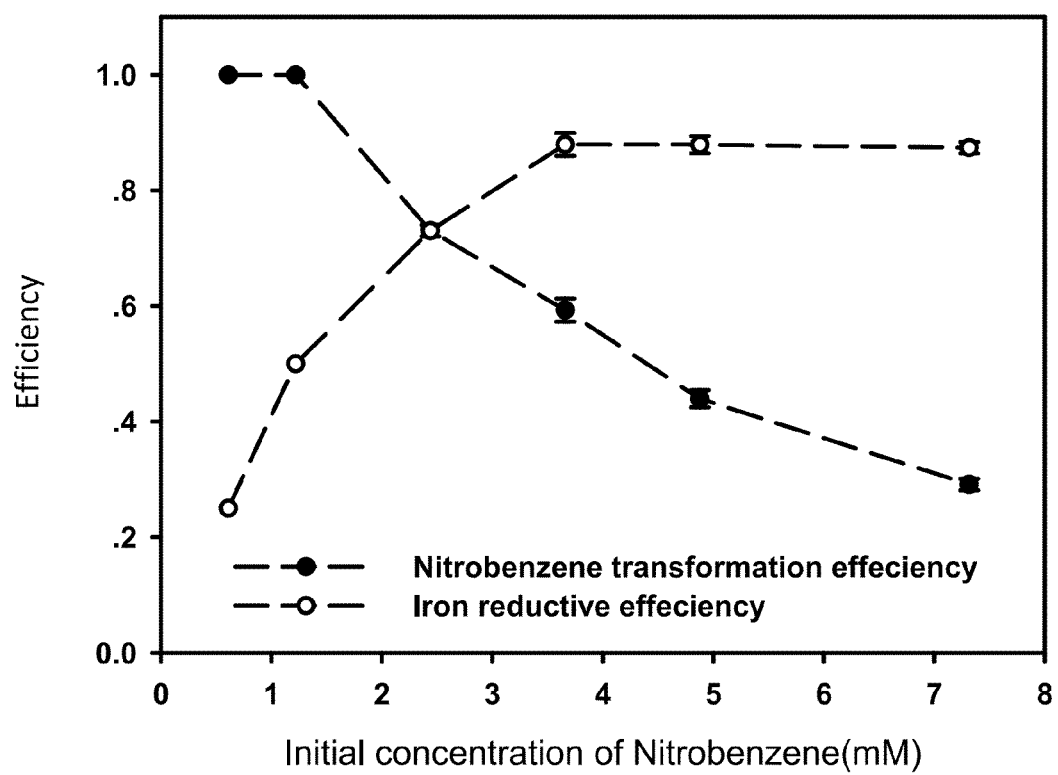
FIG. 5 shows the reduction efficiency of synthesized subnano-sized ZVI templated in smectite interlayers and nitrobenzene transformation efficiency at different initial concentration of nitrobenzene in embodiments of the present invention.

FIG. 5 shows the reduction efficiency of synthesized subnano-sized zero valent iron templated in smectite interlayers and nitrobenzene transformation efficiency at different initial concentration of nitrobenzene. As the results show that all of nitrobenzene can be degraded by ZVI at low concentrations. When concentration of nitrobenzene increased, the transformation efficiency of nitrobenzene decreased, whereas, the reductive efficiency of synthesized subnano-sized zero valent iron increased gradually until attaining to 89%. The data indicated that most of iron (approximately 90%) can be used as reductant to remediate nitrobenzene compound.

A comparison of the reactivity for reduction of nitrobenzene by different iron forms is listed in Table 2. In contrast to the reactivity of known ZVI, the novel clay-templated subnano-sized ZVI particles prepared herein demonstrated a much higher reactivity. It is expected that other types of novel templated subnano-sized ZVI particles will perform as well or better than the particles prepared herein. In this testing, the iron concentration was 0.33 g/L and the initial nitrobenzene concentration was 2.1 mM. The estimated portion of ZVI in clay assemblage which reacted with nitrobenzene was approximately 83% at the $NaBH_4$/Fe(III) ratio of 30. This percentage assumes that all exchangeable Fe(III) is reduced to Fe(0) and available to react with nitrobenzene.

The high reactivity and availability of the clay-templated ZVI is likely attributable to the discrete distribution of iron on the external and interlayer surfaces of SWy-2, which separates the individual reactive Fe(0) domains. The unique smectite layer structure and discrete distribution of negative charges inhibit the growth of large Fe(0) particles (e.g., formation of aggregates) and hence facilitates the formation of very small-sized ZVI even at atomic-sized level (radius of atomic Fe of 1.72 Å) Assuming that the negative charges (820 µmol/g) are evenly distributed on the smectite clay surface (750 m$^2$/g), the clay surface charge density is thereby 1.09 µmol/m$^2$, the calculated distance between adjacent Fe(III) is 15.1 Å.

The total iron content of NaBH$_4$-reduced Fe-SWy-2 was 5.28%, and the structural Fe content was approximately 2.63% leaving ca. 2.65% as ZVI. The theoretical exchangeable Fe$^{3+}$ content was estimated at 1.5% assuming each Fe$^+$ compensates three negative charges. The ZVI content is 1.76 times the theoretical exchangeable Fe$^{3+}$. Therefore, on average, slightly less than two Fe atoms can be assigned to each cation exchange site, suggesting near-single-atom forms of ZVI in the smectite clay interlayers. As the increase of NaBH$_4$/Fe(III) molar ratio, ZVI clusters may be formed. However, the size of ZVI cluster is still within the range of subnano-sized (radius <1.0 nm). Such small discrete atomic-sized ZVI likely explains the observed high reactivity and availability.

(TCP) and phenol using clay-templated Fe$^0$/Pd under the following conditions: [PCP]$_{initial}$=0.075 mM, pH=10. When PCP degraded, TeCP, TCP and phenol were formed over time. As FIG. 5 shows, PCP concentrations decreased over time while TeCP and TCP concentrations initially increased, then decreased. Phenol was the final product, which accumulated as the major product. The total mass is the sum of molar concentrations of reactant and products, which is approximately one. C/C0 is the ratio of concentration at certain time over the initial concentration of PCP.

Figure 7:
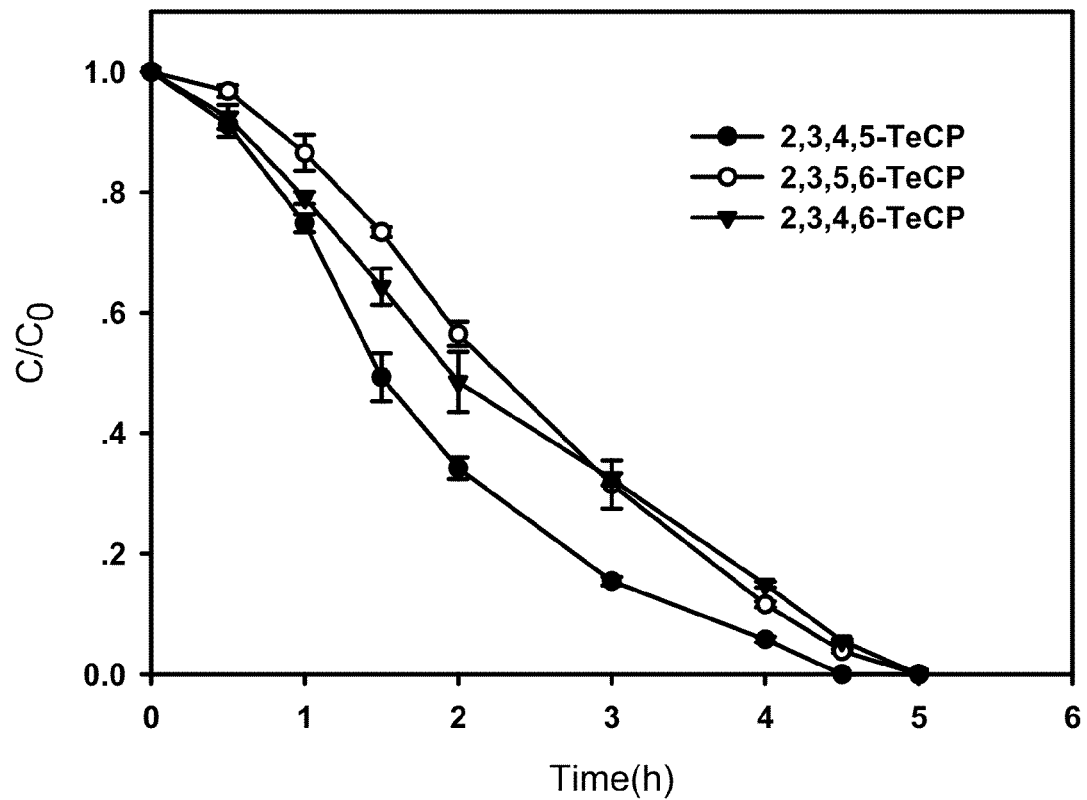
FIG. 7 shows the degradation of 2, 3, 4, 5-TeCP; 2, 3, 5, 6-TeCP; and 2, 3, 4, 6-TeCP over time by clay-templated $Fe^0$/Pd in embodiments of the present invention.

FIG. 7 shows the degradation of 2, 3, 4, 5-TeCP; 2, 3, 5, 6-TeCP; and 2, 3, 4, 6-TeCP over time phenol by clay-templated Fe$^0$/Pd under the following conditions: [TeCP]$_{initial}$=0.075 mM, pH=10.

Figure 8:
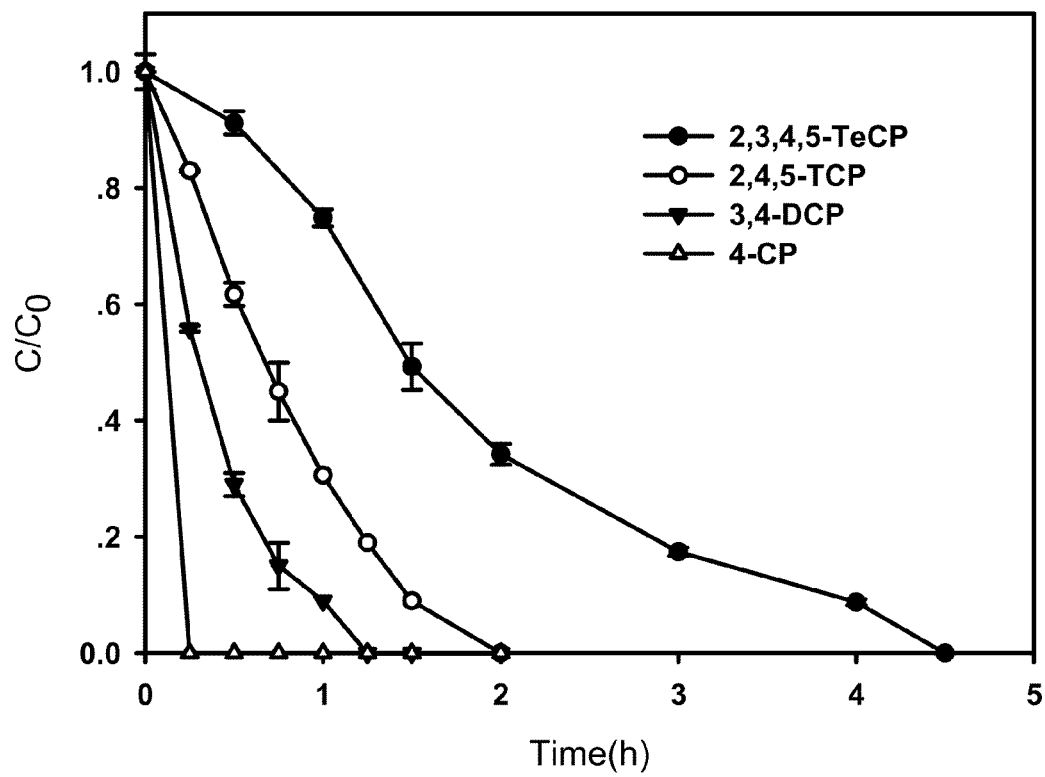
FIG. 8 shows the degradation of 2,3,4,5-TeCP, 2,4,5-TCP, 3,4-DCP and 4-chlorophenol (CP) over time by clay-templated $Fe^0$/Pd in embodiments of the present invention.

FIG. 8 shows the degradation of PCP over time to 2,3,4,5-TeCP; 2,4,5-TCP; 3,4-DCP and 4-chlorophenol (CP) over time by clay-templated Fe/Pd under the following conditions: concentrations are 0.075 mM and pH=10. C/C0 is the ratio of concentration at certain time over the initial concentration of PCP.

Figure 9:
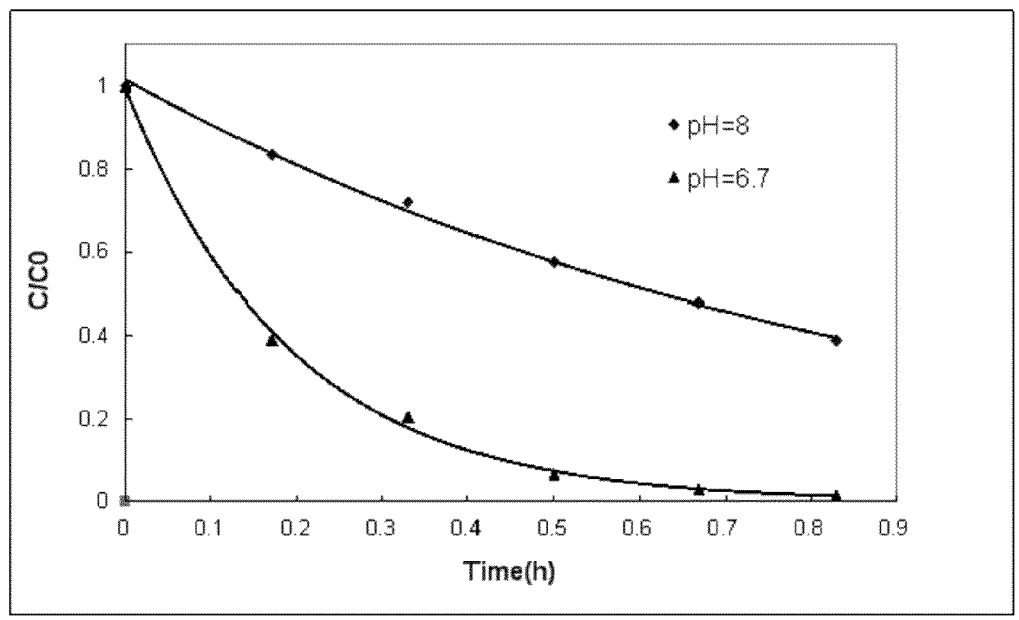
FIG. 9 shows the degradation of PCP over time by clay-templated Fe⁰/Pd at pH of 8 and 6.7 in embodiments of the present invention.
Figure 10:
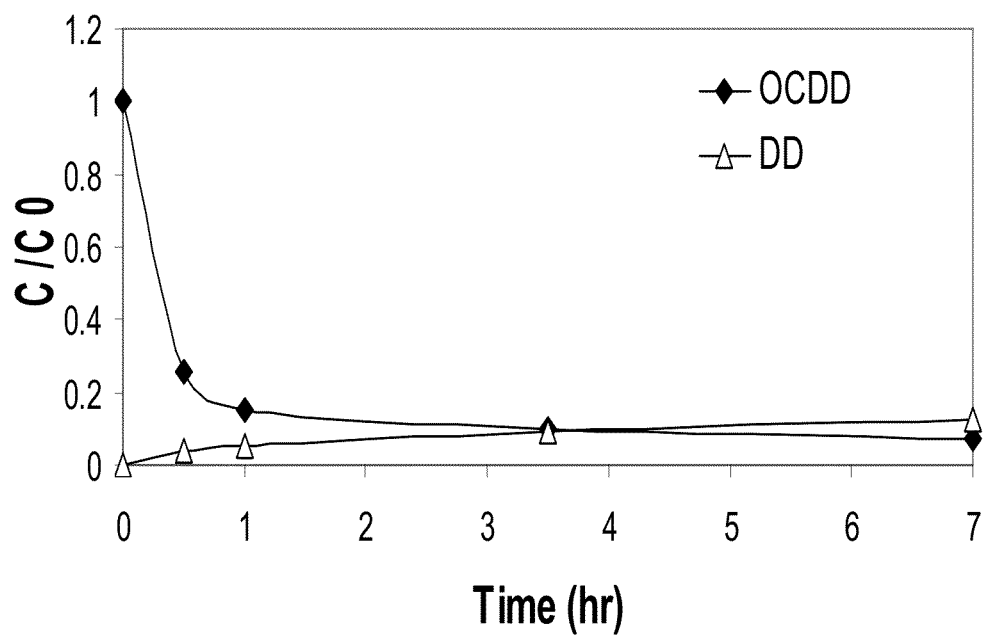
FIG. 10 shows the degradation of octachlorodibenzo-p-dioxin (OCDD) and formation of dibenzo-p-dioxin (DD) by clay-templated Fe⁰/Pd in embodiments of the present invention.

FIG. 9 shows the degradation of PCP over time by clay-templated Fe/Pd at a pH of 8 and 6.7. [PCP]$_{initial}$=0.075 mM FIG. 10 shows the degradation of octachlorodibenzo-p-dioxin (OCDD) by clay-templated Fe/Pd and formation of dibenzo-p-dioxin (DD) under the following conditions: [OCDD]$_{initial}$=1.14 ppm, 1:1 water/propanol background.

TABLE 2

Comparison of reactivity for reduction of nitrobenzene by different iron forms

| Type | Compound | Cross-section of iron particle | Reactive iron concentration (g/L) | Nitrobenzene Initial concentration (mM) | Reaction time |
|---|---|---|---|---|---|
| Micro-sized ZVI | nitrobenzene | 0.84~1 mm$^a$ | 33.3$^a$ | | ~90% nitrobenzene reduced in 1 hour$^a$ |
| Nano-sized ZVI | nitrobenzene | 1~200 nm$^b$ | 5$^b$ | 0.0812$^b$ | Most of nitrobenzene reduced in 5 minutes$^b$ |
| Structural Fe(II) in ferruginous smectite (SWa-1) | 2-acetylnitrobenzene | / | 0.35$^c$ | 0.05$^c$ | ~90% 2-acetylnitrobenzene reduced in 2 hours$^c$ |
| Fe-SWy-2 after NaBH$_4$ reduction (NaBH$_4$/Fe(III) = 30) | nitrobenzene | ≤5 Å | 0.33 | 2.1 | ~80% nitrobenzene reduced within 1 minute |

$^a$Agrawal, A.; Tratnyek, P. G. Reduction of nitro aromatic compounds by zero-valent iron metal. *Environ. Sci. Technol.* 1996, 30, 153-160.
$^b$Choe, S.; Lee, S. H.; Chang, Y. Y.; Hwang, K. Y.; Khim, J. Rapid reductive destruction of hazardous organic compounds by nanoscale Fe$^0$. *Chemosphere* 2001, 42, 367-372.
$^c$Neumann, A.; Hofstetter, T. B.; Lussi, M.; Cirpka, O. A.; Petit, S.; Schwarzenbach, R. P. Assessing the redox reactivity of structural iron in smectites using nitroaromatic compounds as kinetic probes. *Environ. Sci. Technol.* 2008, 42, 8381-8387.

Example 2

The novel materials described herein were tested for the dechlorination of two chlorinated aromatic compounds, namely chlorophenols and octachlorodibenzo-p-dioxin. For these experiments, unless, otherwise noted, materials and methods as described in Example 1 were used. To further accelerate the dechlorination process, palladium (Pd) was added as a catalyst in the clay and the clay synthesis method was modified accordingly. Specifically, after Fe(III)-SWy-2 was prepared, the clay was mixed with 1 mM Pd(NO$_3$)$_2$ twice, then washed using Milli-Q water twice. Thereafter, the previously described preparation was followed. Palladium loading was 0.65 mg Pd/g clay.

Figure 6:
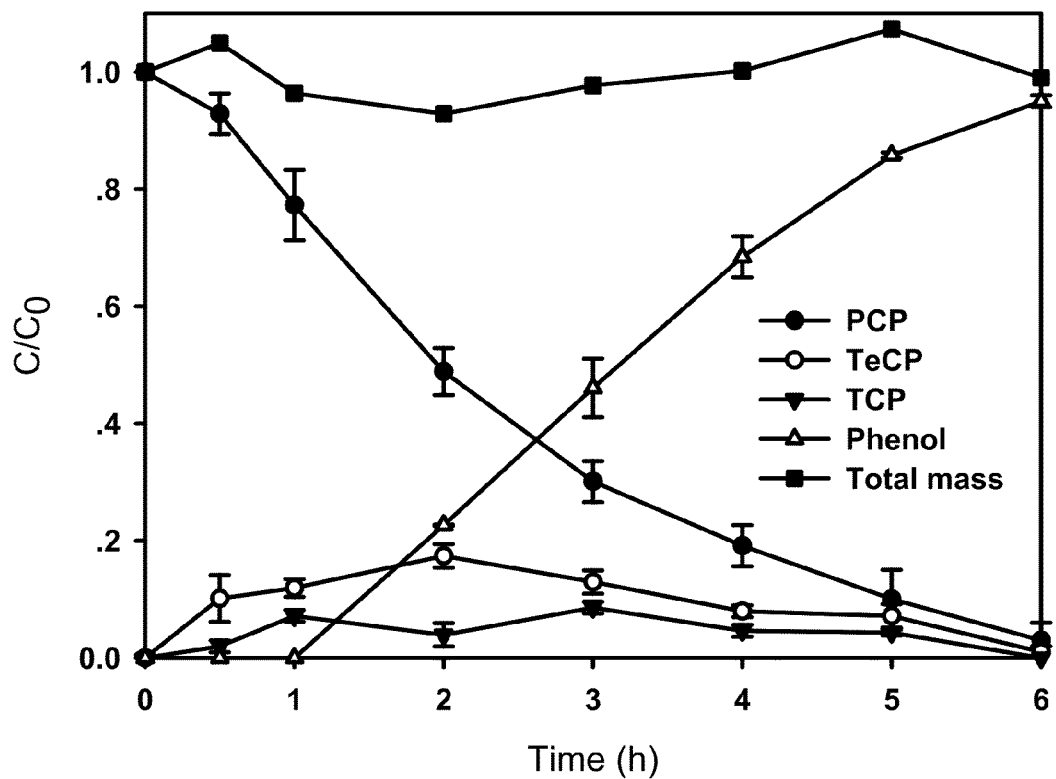
FIG. 6 shows the degradation of pentachlorophenol (PCP) over time to tetrachlorophenol (TeCP), tricholorphenol (TCP) and phenol with use clay-templated $Fe^0$/Pd in embodiments of the present invention.

FIG. 6 shows the degradation of pentachlorophenol (PCP) over time to tetrachlorophenol (TeCP), tricholorphenol These results showed here indicate that smectite-templated ZVI manifested a high reactivity with many chlorinated organic compounds, and is expected useful in dechlorination applications.

Example 3

Figure 11:
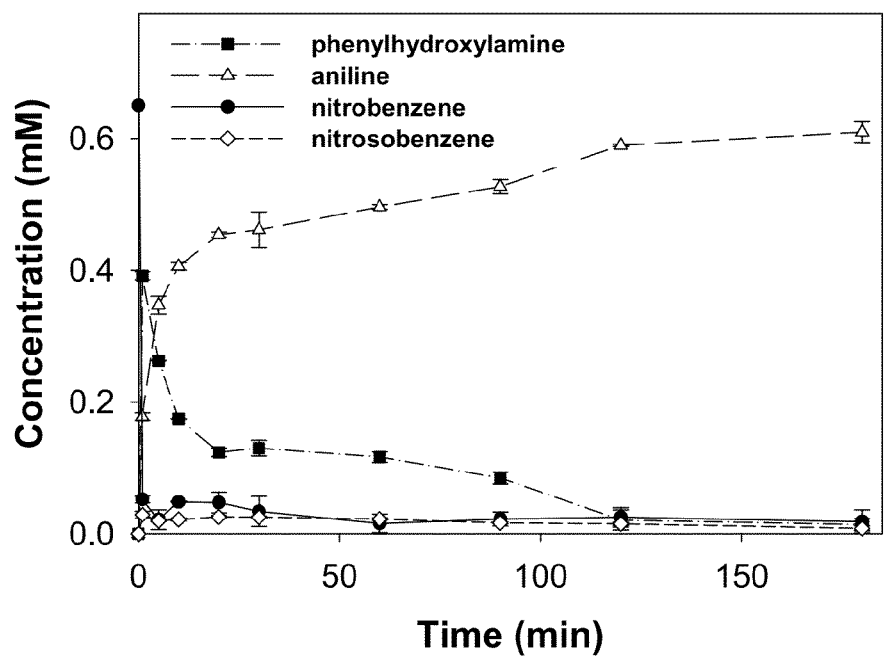
FIG. 11 shows reduction of aqueous phase nitrobenzene by subnano-sized ZVI templated in smectite interlayers in embodiments of the present invention.

Unless otherwise noted, this testing followed the protocol of Example 1. FIG. 11 shows the reduction of aqueous phase nitrobenzene by subnano-sized ZVI templated in smectite interlayers. Experimental conditions were as follows: initial nitrobenzene, clay and interlayer iron concentrations of 0.65 mM, 12.6 and 0.33 g/L, respectively. Experiments were conducted at room temperature (approximately 23° C.). Error bars are the standard deviations of triplicate analyses.

FIG. 11 shows that the degradation of nitrobenzene occurred rapidly. Within the first minute, at the first sampling, more than 90% of nitrobenzene was reduced and the major intermediate was phenylhydroxylamine. As the reaction proceeded, phenylhydroxylamine was reduced to aniline, which accumulated as the major reductive product. After three hours, aniline accounted for about 94% of the original nitrobenzene (0.65 mM), in addition to a small amount of nitrosobenzene (approximately 4%).

Figure 12:
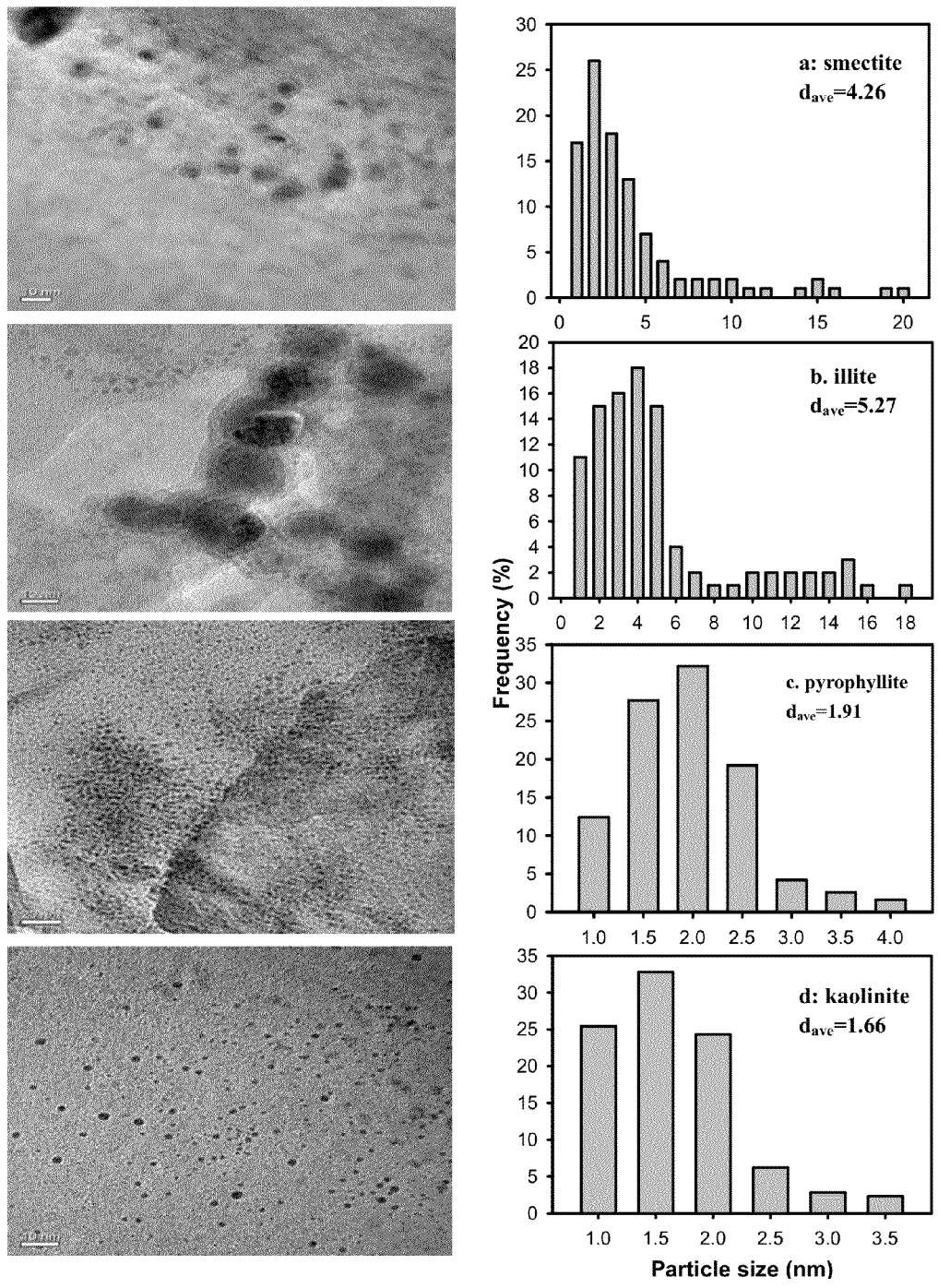
FIG. 12 shows transmission electron microscopy images and particle size distributions of the synthesized zero-valent irons associated with (a) smectite, (b) illite, (c) pyrophyllite, and (d) kaolinite in embodiments of the present invention.

FIG. 12 shows that the ZVI particles on smectite external surfaces were highly dispersed with particle size ranging from approximately one (1) to approximately 20 nm. Most particles fell within the range of about one (1) to seven (7) nm. A minor fraction of the particles were found with sizes >14 nm which were partially chained together. The average diameter of ZVI particles on smectite external surfaces was approximately 4.26 nm ("a: smectite"). The subnano-sized ZVI particles residing on illite external surfaces manifested a similar size range but with a larger average diameter of approximately 5.27 nm ("b: illite"). Interestingly, the particle sizes of the ZVI on kaolinite and pyrophyllite surfaces were much smaller than ZVI clusters on smectite and illite external surfaces. ZVI particles formed on the kaolinite surfaces were small and evenly distributed with a more narrow size range from about one (1) to about four (4) nm, with an average particle diameter of 1.66 nm ("d: kaolinite"). Pyrophyllite had a similar pattern of ZVI size distribution and average diameter as that observed for kaolinite ("c: pyrophyllite"). The particle diameters of ZVI on pyrophillite ranged between 1 to 4 nm, and the average diameter was 1.91 nm.

Figure 13:
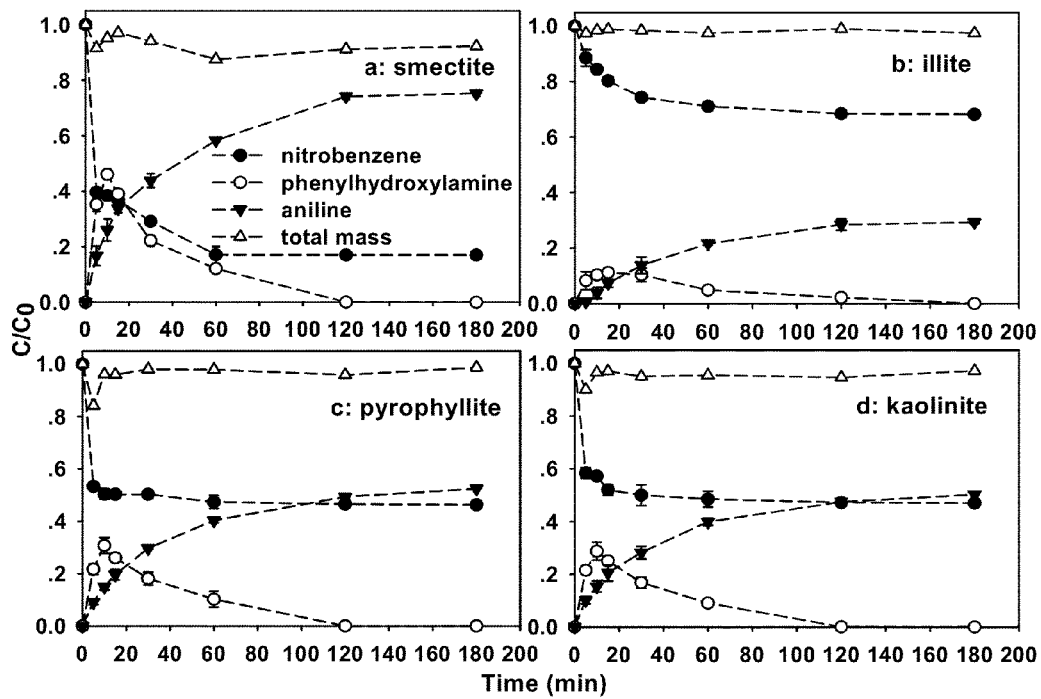
FIG. 13 shows reaction kinetics of nitrobenzene reductive transformation with zero valent iron associated with (a) smectite, (b) illite, (c) pyrophyllite, and (d) kaolinite in embodiments of the present invention.

As FIG. 13 shows, the reduction of nitrobenzene was used to probe the ZVI reactivity by normalizing the amount of ZVI associated with smectite, illite, kaolinite and pyrophyllite clays. The loss of nitrobenzene and formation of intermediate phenylhydroylamine and product aniline expressed as molar ratio of nitrobenzene concentration at any time (C) to that at the beginning of the reaction ($C_0$) is presented as a function of reaction time (FIG. 13). The sums of molar ratios were >90% during the reaction periods indicating that the systems achieved a good mass balance. It was noted that nitrobenzene concentrations decreased rapidly, and reached a plateau after approximately 60 min. After the first 60 min of reaction, approximately 82%, 55%, 56%, and 30% of initially added nitrobenzene was reduced by the ZVI associated with smectite, kaolinite, pyrophyllite and illite clays, respectively. The disappearance of nitrobenzene in the systems followed the order of smectite>pyrophyllite >kaolinite>illite, and manifested an inversed relationship with the diameter of ZVI clusters. Overall, the order of reaction rate and magnitude was inversely correlated to the size of ZVI associated with clay minerals.

The error bar represents the standard deviation. The initial nitrobenzene concentration ($C_0$) was 2.4 mM. Zero-valent iron content was maintained at 0.4 g $L^{-1}$, and the corresponding clay concentrations were 13.3, 102, 49.3, and 22.5 g $L^{-1}$ for smectite, kaolinite, pyrophyllite, and illite, respectively.

Figure 14:
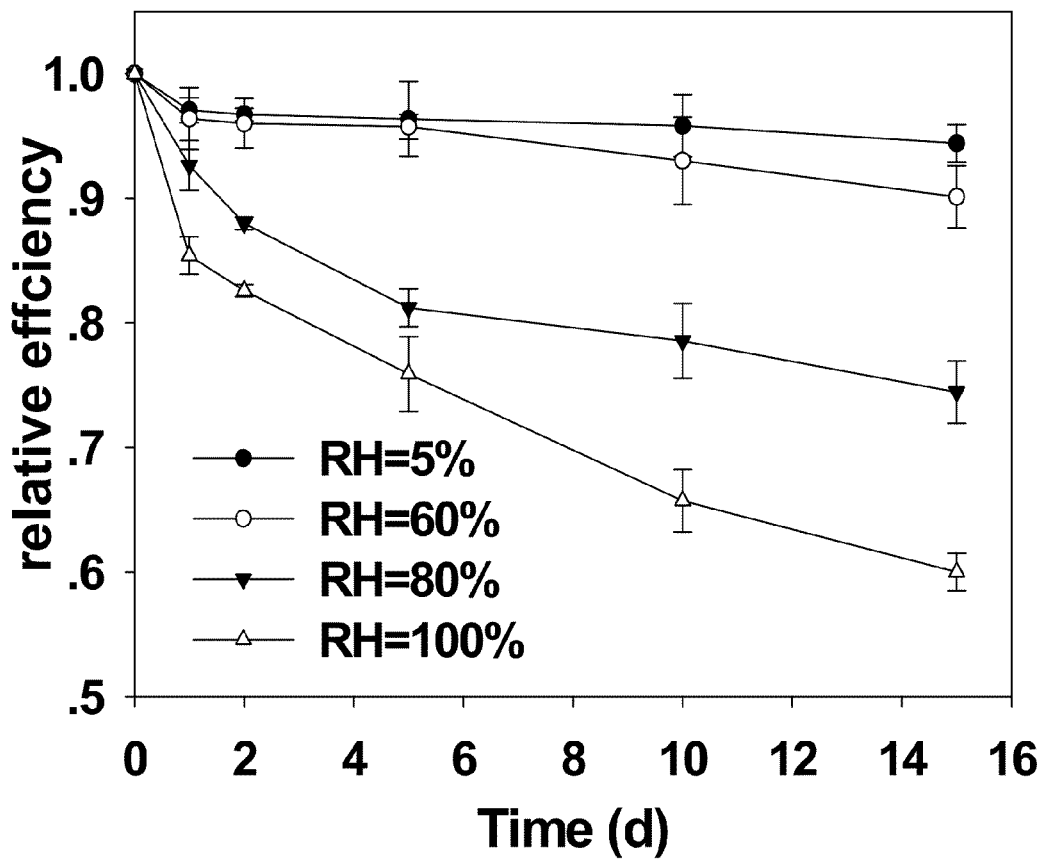
FIG. 14 shows the relative reaction efficiency of ZVI with nitrobenzene as a function of exposure time (days) to ambient air environment under several relative humidity (RH) in embodiments of the present invention.

As FIG. 14 shows, the relative reaction efficiency of ZVI with nitrobenzene was maintained at >90% after exposing to ambient air environment with the relative humidity (RH) <60% for two weeks. Exposure to the RH>80% for 2 weeks resulted in the loss of ZVI reactivity >30%. We discovered that intercalation of ZVI between smectite layers preserves ZVI reactivity from corrosion. These results demonstrate that, in contrast to conventional ZVI particles, the novel ZVI particles described herein have reduced corrosion due to their intercalation in clay interlayers to retain their reactivity.

CONCLUSION

Novel 2:1 aluminosilicate clays containing subnano-sized ZVI particles and novel clay-templated subnano-sized ZVI particles are provided. Novel methods for synthesizing subnano-sized zero-valent iron (ZVI) using 2:1 aluminosilicate clay as a template is provided. A novel method of producing clays containing these materials is also provided.

The unique structure of 2:1 aluminosilicate clay, such as a smectite clay, in which isolated exchangeable Fe(III) cations reside at or near the discrete sites of structural negative charges, prevents or reduces the agglomeration of ZVI resulting in the formation of sub-nanosized iron particles on the clay surfaces.

The extremely small size of the novel clay-templated ZVI particles described herein (≤5 Å cross-section) results in significantly enhanced reactivity and efficiency as compared to previously reported forms of ZVI, including nano-sized particles. The clay-templated particles and 2:1 aluminosilicate clays described herein will also likely intercalate many inorganic and organic contaminants such as Cr(VI), nitroaromatic compounds, trichloroethene/perchloroethene, polychlorinated byphenyls and dioxins. It is expected that smectite-intercalated subnano-sized ZVI particles, as described herein, will significantly enhance the reduction of these contaminants due to an increased contact probability between ZVI and the contaminants in clay interlayers and enhanced reactivity of smaller-sized particles.

Since 2:1 aluminosilicate layers are commonly found in soils, subsoils, aquifer materials and sediments, the novel ZVI particles described herein have further utility as an in situ remediation technology. In one embodiment, the novel ZVI particles are used as a component of a reactive cap or wall. Similarly, such reactive caps could also be used to contain and remediate contaminated sediments, i.e., in containment treatments.

These and other applications could potentially harness several advantageous properties of 2:1 aluminosilicate clays, allowing them to function simultaneously as a hydraulic barrier, an adsorbent, to degrade contaminants via reduction with ZVI. Thus, synthesized clay-templated ZVI could find utility as a component of reactive barriers to degrade chlorinated solvents, nitrobenzene and other environmental persistent contaminants in a variety of settings.

All of the publications, including any and all articles, patents and published patent applications are incorporated by reference herein, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. For example, although the invention has been described in terms of a particle of five (5) Å or less, it is also possible that larger subnano-sized particles having a cross section larger than five (5) Å would also perform satisfactorily. This application is intended to cover any adaptations or variations of the present subject matter. Therefore, it is manifestly intended that embodiments of this invention be limited only by the claims and the equivalents thereof.

What is claimed is:

1. A product comprising a 2:1 aluminosilicate clay having negative charge sites, the 2:1 aluminosilicate clay containing subnano-sized zero valent iron (ZVI) particles distributed on clay surfaces.

2. The product of claim 1 wherein some or all of the ZVI particles have a cross-section of five (5) angstroms or less.

3. The product of claim 1 wherein the 2:1 aluminosilicate clay is a swelling clay.

4. The product of claim 3 wherein the swelling clay is smectite.

5. The product of claim 4 wherein the smectite is montmorillonite.

6. The product of claim 1 wherein the 2:1 aluminosilicate clay is a non-swelling clay.

7. The product of claim 6 wherein the non-swelling clay is kaolinite, pyrophyllite, illite or combinations thereof.

8. The product of claim 1 wherein each particle comprises one or more iron atoms.

9. The product of claim 1 wherein the subnano-sized ZVI particles are intercalated in clay interlayers.

10. A particle comprising a plurality of clay-templated subnano-sized zero valent iron (ZVI) particles, wherein the clay is a 2:1 aluminosilicate clay.

11. The particle of claim 10 wherein some or all of the ZVI particles have a cross-section of five (5) angstroms or less.

12. The particle of claim 10 wherein the 2:1 aluminosilicate clay is a smectite.

13. The particle of claim 10 wherein the smectite is montmorillonite.

14. The particle of claim 10 having a reactivity of greater than 90% for at least 14 days.

15. A method comprising:
providing a 2:1 aluminosilicate clay template comprising layers, each layer having a substantially planar surface, wherein structural negative charges are embedded throughout each layer, embedded on each substantially planar surface, or a combination thereof;
neutralizing the structural negative charges by combining the 2:1 aluminosilicate clay with exchangeable iron cations to produce iron-containing 2:1 aluminosilicate clay; and
reducing each of the iron-containing neutral charges with a reducing agent to produce subnano-sized zero valent iron (ZVI) particles.

16. The method of claim 15 wherein some or all of the particles have a cross section of five (5) angstroms or less.

17. The method of claim 15 further comprising combining a 2:1 aluminosilicate clay with a cation to produce a homoionic 2:1 aluminosilicate clay template.

18. The method of claim 15 wherein the wherein the 2:1 aluminosilicate clay is a smectite.

19. The method of claim 15 wherein the exchangeable iron cations are Fe(III) cations.

20. The method of claim 15 wherein the exchangeable iron cations are Fe(II) cations and the method further comprises performing the neutralizing and reducing steps in an anaerobic chamber.

21. The method of claim 15 wherein the subnano-sized ZVI particles have a cross section between about 3.4 angstroms and five (5) angstroms.

22. The method of claim 20 wherein at least one of the subnano-sized ZVI particles is a single iron atom having a radius of 1.72 angstroms.

23. The method of claim 15 wherein the reducing agent is a borohydride salt.

24. The method of claim 23 wherein the borohydride salt is sodium borohydride or potassium borohydride.

25. The method of claim 15 wherein the iron-containing 2:1 aluminosilicate clay is in a 2:1 aluminosilicate slurry having a pH and the method further comprises adjusting the pH to a level sufficient to prevent dissolution of the 2:1 aluminosilicate clay.

26. The method of claim 25 wherein the reducing agent is sodium borohydride and the pH is adjusted to about 2.

27. The method of claim 15 wherein the method further comprising removing excess reducing agent.

28. The method of claim 15 wherein the combining step comprises saturating the clay with ZVI particles.

29. A product made according to the method of claim 15.

30. The method of claim 15 further comprising mixing the iron saturated clay with palladium or nickel.

31. The method of claim 30 wherein the palladium is $Pd(NO_3)_2$.

32. A product made according to the method of claim 31.

33. A method comprising reducing nitrobenzene with subnano-sized ZVI particles, each particle having a cross-section of five (5) angstroms or less.

34. The method of claim 33 wherein at least 80% of the nitrobenzene is degraded within one minute.

35. The method of claim 33 wherein the molar ratio of $NaBH_4$ to Fe(III) is 30.

36. The method of claim 32 wherein at least 90% of the nitrobenzene is degraded within one minute.

* * * * *

UNITED STATES PATENT AND TRADEMARK OFFICE
CERTIFICATE OF CORRECTION

PATENT NO. : 8,633,133 B2  Page 1 of 1
APPLICATION NO. : 12/915428
DATED : January 21, 2014
INVENTOR(S) : Hui Li, Cheng Gun and Stephen A. Boyd It is certified that error appears in the above-identified patent and that said Letters Patent is hereby corrected as shown below:

In the Specification

Pat col. 3/Line 37: Error reads as "conclusion" and should read as "conclusion."

Pat col. 3/Line 57: Error reads as "relatives" and should read as "relative"

Pat col. 6/Line 59: Error reads as "at least then fold" and should read as "at least ten fold"

Pat col. 8/Line 14: Error reads as "4°C. as" and should read as "4°C as"

Pat col. 8/Line 57: Error reads as "deposited I" and should read as "deposited in"

Pat col. 10/Line 45: Error reads as "20" and should read as "2θ"

Pat col. 12/Line 49: Error reads as "results show that all" and should read as "results show, all"

Pat col. 14/Line 24: Error reads as "Fe/Pd" and should read as "Fe$^{0}$/Pd"

Pat col. 14/Line 27: Error reads as "Fe/Pd" and should read as "Fe$^{0}$/Pd"

Signed and Sealed this
First Day of July, 2014

Michelle K. Lee
*Deputy Director of the United States Patent and Trademark Office*